United States Patent [19]

Shalaby et al.

[11] Patent Number: 5,665,702
[45] Date of Patent: Sep. 9, 1997

[54] IONIC MOLECULAR CONJUGATES OF N-ACYLATED DERIVATIVES OF POLY(2-AMINO-2-DEOXY-D-GLUCOSE) AND POLYPEPTIDES

[75] Inventors: Shalaby W. Shalaby, Anderson, S.C.; Steven A. Jackson, Holliston, Mass.; Francis Ignatious, Milford, Mass.; Jacques-Pierre Moreau, Upton, Mass.

[73] Assignee: Biomeasure Incorporated, Milford, Mass.

[21] Appl. No.: 468,947

[22] Filed: Jun. 6, 1995

[51] Int. Cl.$^6$ ................................. A61K 38/12
[52] U.S. Cl. ................................. 514/9; 514/11
[58] Field of Search ................................. 514/9, 11

[56] References Cited

U.S. PATENT DOCUMENTS

| | | | |
|---|---|---|---|
| 4,675,189 | 6/1987 | Kent et al. | 424/468 |
| 4,767,628 | 8/1988 | Hutchinson | 424/426 |
| 5,271,945 | 12/1993 | Yoshioka et al. | 424/489 |

FOREIGN PATENT DOCUMENTS

| | | | |
|---|---|---|---|
| 0482649 | 4/1992 | European Pat. Off. | |
| 0 482 649 A2 | 4/1992 | European Pat. Off. | C08B 37/08 |
| 0 486 959 A1 | 5/1992 | European Pat. Off. | A61K 9/16 |
| 0 525 813 A1 | 2/1993 | European Pat. Off. | A61K 47/36 |
| 0 544 000 A1 | 6/1995 | European Pat. Off. | C08B 37/08 |

OTHER PUBLICATIONS

Domard et al., "Preparation and Characterization of Fully Deacetylated Chitosan", Int. J. Biol. Macromol., 5:49–52, 1983.

Jameela et al., "Cross–Linked Chitosan Microspheres as Carriers for Prolonged Delivery of Macromolecular Drugs", J. Biomater. Sci. Polymer Edn., 6:621–632, 1994.

Mima et al., "Highly Deacetylated Chitosan and Its Properties", Journal of Applied Polymer Sciences, 28:1909–1917, 1983.

Song et al., "Pharmacokinetic Characteristics and Antitumor Activity of the N–Succinyl–chitosan–Mitomycin C . . . ", Biol. Pharm. Bull, 16:48–54, 1993.

Song et al., "Synthesis and Drug–Release Characteristics of the Conjugates of Mitomycin C with N–Succinyl–chitosan and Carboxymethyl–chitin", Chem. Pharm. Bull, 40:2822–2825, 1992.

Tokura et al., "Induction of Drug Specific Antibody and the Controlled Release of Drug by 6–0–Carboxymethyl- -Chitin", Journal of Controlled Release, 28:235–241, 1994.

Watanabe et al., "6–0–Carboxymethyl–Chitin (CM–chitin) as a Drug Carrier", Chem. Pharm. Bull, 38:506–509, 1990.

*Primary Examiner*—Edward J. Cain
*Attorney, Agent, or Firm*—Fish & Richardson, P.C.; William E. McGowan

[57] ABSTRACT

A copolymer comprising an N-acylated derivative, and a composition comprising said copolymer and a polypeptide, said polypeptide comprising at least one effective ionogenic amine, wherein at least 50 percent, by weight, of said polypeptide present in said composition is ionically bound to said polymer.

14 Claims, No Drawings

IONIC MOLECULAR CONJUGATES OF N-ACYLATED DERIVATIVES OF POLY(2-AMINO-2-DEOXY-D-GLUCOSE) AND POLYPEPTIDES

BACKGROUND OF THE INVENTION

Polymer drug delivery systems have been developed for the controlled release of pharmaceutical polypeptides. For example, synthetic polyesters such as poly(DL-lactic acid), poly(glycolic acid), poly(lactic-glycolic acid), and poly(ε-caprolactone) have been used in the form of microcapsules, films, or rods to release biologically active polypeptides. See e.g., U.S. Pat. Nos. 4,767,628 and 4,675,189 and PCT Application No. WO 94/00148.

In addition to the synthetic polymeric chains, natural polymers and their derivatives have been used as components in similar sustained release compositions that dissociate by enzymatic degradation. One example of such natural polymers are those based on chitin, a poly(N-acetylglucosamine). However, since chitin is water insoluble, others have examined solubilizable derivatives which are based primarily on a partially deacetylated chitin, e.g., chitosan. See e.g., Sanford, P. A. et al., Eds., Advances in Chitin & Chitosan (1992). Although chitosan can be found in some fungi, the production of biodegradable chitosan is generally performed synthetically. See Mima, et. al., J. Appl. Polym. Sci. 28:1909–1917 (1983). Synthetic derivatives of chitosan have also been prepared to alter the polymer's in vivo biological characteristics. See Muzzarelli, et al., Carbohydrate Res. 207:199–214 (1980).

The use of chitin, as well as chitin derivatives, has been proposed in a number of drug delivery systems. See, e.g., European Patent Application Nos. 486,959, 482,649, 525, 813 A1, and 544,000 A1; and U.S. Pat. No. 5,271,945.

SUMMARY OF THE INVENTION

In one aspect, the present invention features a copolymer including an N-acylated derivative of poly(2-amino-2-deoxy-D-glucose), wherein between 1 and 50 percent of the free amines of the poly(2-amino-2-deoxy-D-glucose) are acylated with a first acyl group, the first acyl group is $COE_1$ where $E_1$ is selected from the group consisting of $C_{3-33}$ carboxyalkyl, $C_{3-33}$ carboxyalkenyl, $C_{7-39}$ carboxyarylalkyl, and $C_{9-39}$ carboxyarylalkenyl, and between 50 and 99 percent of the free amines of the poly(2-amino-2-deoxy-D-glucose) are acylated with a second acyl group, the second acyl group is $COE_2$ where $E_2$ is selected from the group consisting of $C_{1-30}$ alkyl, $C_{2-30}$ alkenyl, $C_{6-37}$ arylalkyl, and $C_{8-37}$ arylalkenyl, provided at least one of the free amines of the derivative is acylated with the first acyl group.

The copolymer preferably has a molecular weight of about 3,000 to 90,000 daltons. In other preferred embodiments, over 90 percent of the free amines of the poly(2-amino-2-deoxy-D-glucose) are acylated with either the first acyl group or the second acyl group. Preferably, between 10 and 30 percent of the free amine of the poly(2-amino-2-deoxy-D-glucose) are acylated with the first acyl group. Some of the free hydroxy groups (e.g., between 1 and 30 percent) of the derivative may be acylated with either the first acyl group or the second acyl group.

In a preferred embodiment, the copolymer is of the formula:

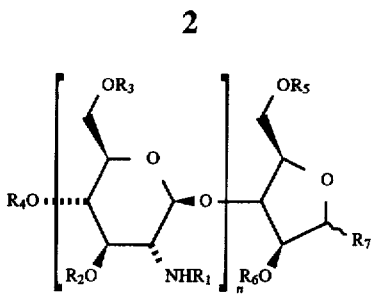

wherein:

$R_1$, for each individual repeat unit, is selected from the group consisting of first acyl group, second acyl group, and H;

$R_2$, for each individual repeat unit, is selected from the group consisting of first acyl group, second acyl group, and H;

$R_3$, for each individual repeat unit, is selected from the group consisting of first acyl group, second acyl group, and H;

$R_4$ is selected from the group consisting of first acyl group, second acyl group, and H;

$R_5$ is selected from the group consisting of first acyl group, second acyl group, and H;

$R_6$ is selected from the group consisting of first acyl group, second acyl group, and H;

$R_7$ is selected from the group consisting of COH and $CH_2OR_8$;

$R_8$ is selected from the group consisting of first acyl group, second acyl group, and H;

n is between 2 and 200; and for between 1 and 50 percent of the repeat units, $R_1$ is first acyl group, and for between 50 and 99 percent of the repeat units, $R_1$ is second acyl group, provided that for at least one of the repeat units, $R_1$ is first acyl group.

The terms $COE_1$ and $COE_2$ stand for $-C=O.E_1$ and $-C=O.E_2$, respectively. The substituents carboxyalkyl, carboxyalkenyl, carboxyarylalkyl, and carboxyarylalkenyl may contain 1–4 carboxylic acid functionalities. Examples of the first acyl group include, but are not limited to, succinyl, 2-($C_{1-30}$ alkyl) succinyl, 2-($C_{2-30}$ alkenyl) succinyl, maleyl, phthalyl, glutaryl, and itaconyl. Examples of the second acyl group include but are not limited to, acetyl, benzoyl, propionyl, and phenylacetyl.

The present invention also features a composition including the above copolymer and a polypeptide, the polypeptide comprising at least one effective ionogenic amine, wherein at least 50 percent, by weight, of the polypeptide present in the composition is ionically bound to the polymer. Preferably, the composition comprises between 5 and 50 percent, by weight, of the polypeptide.

Examples of suitable polypeptides include growth hormone releasing peptide (GHRP), luteinizing hormone-releasing hormone (LHRH), somatostatin, bombesin, gastrin releasing peptide (GRP), calcitonin, bradykinin, galanin, melanocyte stimulating hormone (MSH), growth hormone releasing factor (GRF), growth hormone (GH), amylin, tachykinins, secretin, parathyroid hormone (PTH), enkaphelin, endothelin, calcitonin gene releasing peptide (CGRP), neuromedins, parathyroid hormone related protein (PTHrP), glucagon, neurotensin, adrenocorticothrophic hormone (ACTH), peptide YY (PYY), glucagon releasing peptide (GLP), vasoactive intestinal peptide (VIP), pituitary adenylate cyclase activating peptide (PACAP), motilin, substance P, neuropeptide Y (NPY), TSH and biologically active analogs thereof. The term "biologically active analogs" is used herein to cover naturally occurring, recombinant, and synthetic peptides, polypeptides, and proteins having physiological or therapeutic activity. In general, the term covers all fragments and derivatives of a peptide, protein, or a polypeptide that exhibit a qualitatively similar agonist or antagonist effect to that of the unmodified, or naturally occurring peptide, protein, or polypeptide, e.g., those in which one or more of the amino acid residues occurring in the natural compounds are substituted or deleted, or in which the N- or C-terminal residues has been structurally modified. The term effective ionogenic amine refers to a free amine present on the polypeptide which is capable of forming an ionic bond with the free carboxylic groups on the copolymer.

The release of the polypeptide from the composition may be modified by changing the chemical structure of the composition. Increasing the molecular weight of the polymer will decrease the rate of peptide released from the conjugate. Increasing the number of carboxylic acid groups on the polymer will increase the amount of polypeptide ionically bound to the composition, and consequently, increase the amount of release of the peptide from the conjugate.

The release of the polypeptide may be further modulated through (a) treating the composition with soluble salts of divalent or polyvalent metallic ions of weak acids (e.g., calcium, iron, magnesium, or zinc); (b) coating the particles with a thin, absorbable layer made of a glycolide copolymer or silicone oil in a spherical, cylindrical, or planar configuration; or (c) microencapsulating the composition in an absorbable glycolide copolymer. In one embodiment, the composition comprises between 0.01 and 20 percent, by weight, of a polyvalent metal.

Depending on the choice of polypeptide, the compositions can be used to treat any number of disorders. For example, somatostatin, bombesin, GRP, LHRH, and analogs thereof, have been shown to treat various forms of cancer. Growth factors such as GH, GRF, and GHRP, and analogs thereof, have been shown to stimulate growth in both adolescents and the elderly. Calcitonin, amylin, PTH, and PTHrP, and analogs thereof, have been shown to treat osteoporosis and other bone disorders.

The compositions are designed for parenteral administration, e.g., intramuscular, subcutaneous, intradural, or intraperitoneal injection. Preferably, the compositions are administered intramuscularly.

The compositions of the invention can be in the form of powder or a microparticle to be administered as a suspension with a pharmaceutically acceptable vehicle (e.g., water with or without a carrier substance such as mannitol or polysorbate). The compositions may also be compounded in the form of a rod for parenteral implantation using a trocar, e.g., intramuscular implantation.

The dose of the composition of the present invention for treating the above-mentioned diseases or disorders varies depending upon the manner of administration, the age and the body weight of the subject, and the condition of the subject to be treated, and ultimately will be decided by the attending physician or veterinarian. Such an amount of the composition as determined by the attending physician or veterinarian is referred to herein as a "therapeutically effective amount."

In another aspect, the present invention features a process of synthesizing a copolymer, the process comprising the steps of: reacting chitosan with a weak acid to produce a lower molecular weight polysaccharide; reacting between 1 and 50 percent of the free amines of the lower molecular weight polysaccharide with a first acylating agent, the first acylating agent selected from the group consisting of $C_4$–$C_{34}$ polycarboxyalkane, $C_4$–$C_{34}$ polycarboxyalkene, $C_8$–$C_{40}$ polycarboxyarylalkane, $C_{10}$–$C_{40}$ polycarboxyarylalkene, or an acylating derivative thereof; and reacting between 50 and 100 percent of the free amine of the lower molecular weight polysaccharide with a second acylating agent, the second acylating agent selected from the group consisting of $C_{2-31}$ monocarboxyalkane, $C_{3-31}$ monocarboxyalkene, $C_{7-38}$ monocarboxyarylalkane, $C_{9-35}$ monocarboxyarylalkene, or an acylating derivative thereof. The reaction of the lower molecular weight polysaccharide with both the first acylating agent and the second acylating agent may be measured with an amine detecting agent (e.g., fluorescamine) to ensure that between 1 and 50 percent of the free amines of the lower molecular weight polysaccharide are acylated with the first acylating agent and between 50 and 99 percent of the free amines of the lower molecular weight polysaccharide are acylated with the second acylating agent. See, e.g., Bailey, P. D., An Introduction to Peptide Chemistry (Wiley, N.Y.)(1990); Oppenheimer, H. et al. Archives Biochem. Biophys. 120:108–118 (1967); Stein, S, Arch. Biochem. Biophys. 155:203–212 (1973).

Reacting chitosan with the weak acid (e.g., nitrous acid) cleaves the polymer, thereby reducing its molecular weight (e.g., 2,500–80,000 daltons). In preferred embodiments, the first acylating group and the second acylating agent are reacted with the lower molecular weight polysaccharide successively, e.g., either the first acylating agent is reacted before the second acylating agent is reacted or the second acylating agent is reacted before the first acylating agent or simultaneously. As a result of the acylation of the free amines, some of the free hydroxy groups of the lower molecular weight polysaccharide may be acylated. The extent of the acylation of the free hydroxy groups may be altered by changing the pH or the solvents or agents used during the acylation reactions, or the acylating agents used.

Examples of acylating derivatives include, but are not limited to, anhydrides and N-acylated heterocycles (e.g., imidazoles and pyrazoles). See e.g., Bodansky, et al., The Practice of Peptide Synthesis, 87–150 (Springer-Verlag, 1984). The agents polycarboxyalkane, polycarboxyalkene, polycarboxyarylalkane, and polycarboxyarylalkene or acylating derivatives thereof contain, or originate from reactants containing, 2–5 carboxylic acid functionalities. The substituents monocarboxyalkane, monocarboxyalkene, monocarboxyarylalkane, and monocarboxyarylalkene contain, or originate from reactants containing, only a single carboxylic acid group. Examples of first acylating agents include, but are not limited to, succinic anhydride, 2-($C_{1-30}$ alkyl)succinic anhydride, 2-($C_{2-30}$ alkenyl)succinic anhydride, maleic anhydride, glutaric anhydride, itaconic anhydride, and phthalic anhydride. Examples of second acylating agents include, but are not limited to, acetic anhydride, benzoic anhydride, N,N'-diacetyl-3,5-dimethylpyrazole, N,N'-diacetylimidazole, phenylacetic anhydride, propionic anhydride, and butyric anhydride.

In yet another aspect, the present invention features a process of synthesizing a composition, the process comprising the steps of: reacting chitosan with a weak acid to produce a lower molecular weight polysaccharide; reacting between 1 and 50 percent of the free amines of the lower molecular weight polysaccharide with a first acylating agent, the first acylating agent selected from the group consisting of $C_4$–$C_{34}$ polycarboxyalkane, $C_4$–$C_{34}$ polycarboxyalkene, $C_8$–$C_{40}$ polycarboxyarylalkane, $C_{10}$–$C_{40}$ polycarboxyarylalkene, or an acylating derivative thereof; reacting between 50 and 100 percent of the free amine of the lower molecular weight polysaccharide with a second acylating agent, the second acylating agent selected from the group consisting of $C_{2-31}$ monocarboxyalkane, $C_{3-31}$ monocarboxyalkene, $C_{7-38}$ monocarboxyarylalkane, $C_{9-35}$ monocarboxyarylalkene, or an acylating derivative thereof; neutralizing the acylated lower molecular weight polysaccharide with a base; and mixing the neutralized lower acylated molecular weight polysaccharide with a polypeptide salt, wherein the polypeptide salt comprises at least one ionogenic amine, to form a polypeptide-copolymer ionic conjugate.

The neutralization step preferably renders the lower molecular weight polysaccharide emulsifiable or soluble in water. In preferred embodiments, the base is an inorganic base (e.g., sodium hydroxide). The polypeptide salt is preferably a weak acid salt (e.g., acetate, lactate, or citrate). The ionic conjugate can be isolated by filtering or by centrifuging the resulting mixture.

The conjugates of the invention can easily be made into injectable microspheres or microparticles, and implantable films or rods, without the need to utilize processing that entails multiphase emulsions. Preferably, the microparticles are manufactured by (a) dissolving the composition in an aprotic, water miscible organic solvent; (b) mixing the organic solvent in water; and (c) isolating the microparticles from the water. In preferred embodiments, the organic solvent is chosen from the group of acetone, acetonitrile, tetrahydrofuran, dimethylformamide, and dimethyl ethylene glycol.

Other features and advantages of the present invention will be apparent from the detailed description and from the claims.

DETAILED DESCRIPTION OF THE INVENTION

The synthesis and use of the copolymer and copolymer-polypeptide ionic conjugates of this invention are well within the ability of a person of ordinary skill in the art. Unless defined otherwise, all technical and scientific terms used herein have the same meaning as commonly understood by one of ordinary skill in the art to which this invention belongs. Also, all publications, patent applications, patents, and other references mentioned herein are incorporated by reference.

It is believed that one skilled in the art can, based on the description herein, utilize the present invention to its fullest extent. The following specific embodiments are, therefore, to be construed as merely illustrative, and not limitative of the remainder of the disclosure in any way whatsoever.

EXAMPLE 1

Depolymerization of Chitosan

Chitosan (Protan, Inc., Portsmouth, N.H.) is dissolved in aqueous acetic acid by stirring with a mechanical stirrer for one day. Nitrogen gas is bubbled through the solution, while an aqueous solution of sodium nitrite is added. After a half hour, the solution is filtered through a sintered glass funnel, under reduced pressure, to remove insoluble particles which are present in the initial chitosan solution. To the filtered solution is added an aqueous solution of NaOH, and the solution is vigorously stirred in methanol to precipitate the polymer. The resulting precipitate is then filtered and alternately washed five times with water and methanol. The precipitate is then dried in a vacuum oven at 60° C. for two days. The depolymerized chitosan comprises an aldehyde group at one end of the chain. The aldehyde end group may be reduced to a primary hydroxyl group by reaction $NaBH_4$. The depolymerized product can be analyzed by gel permeation chromatography (GPC) to determine both its molecular weight and molecular weight distribution (MWD) in comparison to Pullulan reference standards. NMR (nuclear magnetic resonance) and IR (infra-red) studies can be used to determine the amount of N-acetylation on the depolymerized product.

EXAMPLE 2

Partial Succinylation of Depolymerized Chitosan

The depolymerized chitosan from Example 1 is dissolved in 0.1M aqueous acetic acid. To this solution, methanol is added followed by the addition of a solution of succinic anhydride in acetone. The resulting solution is stirred at room temperature for 24 hours. Upon completion of the succinylation, the solution is then precipitated into aqueous acetone. The resulting precipitate is collected by centrifugation and washed five times with methanol. The precipitate is then dissolved in 0.5M KOH and dialyzed against water to a pH of 7. The dialyzed solution is then concentrated under reduced pressure, precipitated in aqueous acetone, and dried in a vacuum oven at 60° C.

To obtain variable levels of succinylation, the extent of the reaction can be monitored as the acylation proceeds by analyzing for number of unacylated amine groups. The number of unacylated amine groups can be determined by quenching a withdrawn sample of the reaction mixture with an amine detecting agent (e.g., flouorescamine). The amount of amine present can be measured spectrophoretically using a standard curve for the copolymer. Additionally, succinic anhydride, thus, can be added successively until the desired acylation percentage is achieved. The exact degree of succinylation of the purified product can be determined using $^1H$ NMR spectroscopy and conductometric titration.

EXAMPLE 3

Acetylation of the N-succinylated chitosan

The partial succinylated sample from Example 2 is dissolved in 0.1M aqueous acetic acid. To this solution, methanol and acetic anhydride is then added, and the reaction mixture is stirred at room temperature for one day. This solution is then precipitated in aqueous acetone. The resulting precipitate is collected by centrifugation and washed five times with methanol. The precipitate is then dissolved in 0.1N KOH and is dialyzed against water to a pH of 7. The final solution is lyophilized to obtain the final product. The acylation procedure can be measured spectrophoretically as discussed in Example 2, and the exact degree of acylation of the purified product can be determined using $^1H$ NMR spectroscopy and conductometric titration.

EXAMPLE 4

Preparation of Poly(N-acyl-D-glucosamine)-peptide ionic conjugate

The N-succinylated chitosan potassium salt of Example 3 is dissolved in water. An aqueous solution of the acetate salt of the somatostatin polypeptide analog SOMATULINE™ (D-Nal-c[Cys-Tyr-D-Trp-Lys-Val-Cys]-Thr-$NH_2$; Kinerton, Dublin, Ireland) is added to the stirred polymer solution. A precipitate forms and is filtered and dried in a vacuum oven at 40° C.

The polypeptide content of the resulting ionic conjugate can be determined by the difference between the amount of initial peptide added and the amount of free residual peptide contained in the filtrate and rinse solution. The peptide content of the resulting ionic conjugate can be determined by comparing the carbon/nitrogen ratio of the initial N-succinylated chitosan with that of the resulting ionic conjugate. GPC analysis can be used to determine molecular weight and MWD, differential scanning calorimetry (DSC) to determine thermal properties and NMR and IR for chemical identity.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A copolymer comprising an N-acylated derivative of poly(2-amino-2-deoxy-D-glucose), wherein between 1 and 50 percent of the free amines of said poly(2-amino-2-deoxy-D-glucose) are acylated with a first acyl group, said first acyl group is $COE_1$ where $E_1$ is selected from the group consisting of $C_{3-33}$ carboxyalkyl, $C_{3-33}$ carboxyalkenyl, $C_{7-39}$ carboxyarylalkyl, and $C_{9-39}$ carboxyarylalkenyl, between 50 and 99 percent of the free amines of said poly(2-amino-2-deoxy-D-glucose) are acylated with a second acyl group, said second acyl group is $COE_2$ where $E_2$ is selected from the group consisting of $C_{1-30}$ alkyl, $C_{2-30}$ alkenyl, $C_{6-37}$ arylalkyl, and $C_{8-37}$ arylalkenyl, provided at least one of the free amines of said poly(2-amino-2-deoxy-D-glucose) is acylated with said first acyl group, and the hydroxy groups of said poly(2-amino-2-deoxy-D-glucose) are free or up to 30 percent of them are acylated with said first acyl group or said second acyl group.

2. A copolymer of claim 1, wherein said copolymer has a molecular weight of about 3,000 to 90,000 daltons as determined by gel permeation chromatography.

3. A copolymer of claim 1, wherein over 90 percent of said free amines of said poly(2-amino-2-deoxy-D-glucose) are acylated with either said first acyl group or said second acyl group.

4. A copolymer of claim 1, wherein between 10 and 30 percent of said free amines of said poly(2-amino-2-deoxy-D-glucose) are acylated with said first acyl group.

5. A copolymer of claim 1, wherein said copolymer is of the formula:

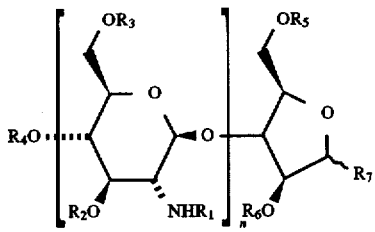

wherein:

$R_1$, for each individual repeat unit, is selected from the group consisting of first acyl group, second acyl group, and H;

$R_2$, for each individual repeat unit, is selected from the group consisting of first acyl group, second acyl group, and H;

$R_3$, for each individual repeat unit, is selected from the group consisting of first acyl group, second acyl group, and H;

$R_4$ is selected from the group consisting of first acyl group, second acyl group, and H;

$R_5$ is selected from the group consisting of first acyl group, second acyl group, and H;

$R_6$ is selected from the group consisting of first acyl group, second acyl group, and H;

$R_7$ is selected from the group consisting of COH and $CH_2OR_8$;

$R_8$ is selected from the group consisting of first acyl group, second acyl group, and H;

n is between 2 and 200; and for between 1 and 50 percent of said units, $R_1$ is first acyl group, and for between 50 and 99 percent of said repeat units, $R_1$ is second acyl group, provided that for at least one of the repeat units, $R_1$ is first acyl group.

6. A copolymer of claim 1, wherein said first acyl group is $COE_1$ where $E_1$ is $C_3$–$C_{33}$ carboxyalkyl.

7. A copolymer of claim 6, wherein said first acyl group is succinyl.

8. A copolymer of claim 7, wherein said second acyl group is acetyl and $R_7$ is COH or $CH_2OH$.

9. A composition comprising said copolymer of claim 1 and a polypeptide, said polypeptide comprising at least one effective ionogenic amine, wherein at least 50 percent, by weight, of said polypeptide present in said composition is ionically bound to said copolymer.

10. A composition of claim 9, wherein said composition comprises between 5 and 50 percent, by weight, of said polypeptide.

11. A composition comprising said copolymer of claim 5 and a polypeptide, said polypeptide comprising at least one effective ionogenic amine, wherein at least 50 percent, by weight, of said polypeptide present in said composition is ionically bound to said copolymer.

12. A composition of claim 11, wherein said composition comprises between 5 and 50 percent, by weight, of said polypeptide.

13. A composition of claim 12, wherein said polypeptide is somatostatin or a somatostatin analog.

14. A composition of claim 10, wherein said first acyl group is succinyl and said second acyl group is acetyl.

* * * * *